US012383335B2

(12) United States Patent
Josse et al.

(10) Patent No.: US 12,383,335 B2
(45) Date of Patent: Aug. 12, 2025

(54) SURGICAL SYSTEM AND METHOD

(71) Applicant: Warsaw Orthopedic, Inc., Warsaw, IN (US)

(72) Inventors: Loïc Josse, Palm Beach Garden, FL (US); Bertrand Peultier, Les Hopitaux Neufs (FR); Julien J. Prevost, Memphis, TN (US); John A. Elliott, Atoka, TN (US); Mark R. Grizzard, Munford, TN (US); Dustin Bobbitt, Olive Branch, MS (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 963 days.

(21) Appl. No.: 17/605,779

(22) PCT Filed: Apr. 23, 2019

(86) PCT No.: PCT/US2019/028612
§ 371 (c)(1),
(2) Date: Oct. 22, 2021

(87) PCT Pub. No.: WO2020/219015
PCT Pub. Date: Oct. 29, 2020

(65) Prior Publication Data
US 2022/0218417 A1 Jul. 14, 2022

(51) Int. Cl.
*A61B 17/70* (2006.01)
*A61B 17/86* (2006.01)
(Continued)

(52) U.S. Cl.
CPC .......... *A61B 34/10* (2016.02); *A61B 17/7032* (2013.01); *A61B 17/7035* (2013.01);
(Continued)

(58) Field of Classification Search
CPC ............ A61B 17/7074; A61B 17/7077; A61B 17/7076; A61B 17/7079; A61B 17/708
See application file for complete search history.

(56) References Cited

U.S. PATENT DOCUMENTS

| 6,030,402 A | 2/2000 | Thompson et al. |
| 6,139,493 A | 10/2000 | Koros et al. |

(Continued)

FOREIGN PATENT DOCUMENTS

| CN | 101489497 | 7/2009 |
| CN | 108498152 | 9/2018 |

(Continued)

OTHER PUBLICATIONS

Official Action for China Patent Application No. 202080099220.8, dated Nov. 8, 2024, 10 pages.
(Continued)

*Primary Examiner* — Eduardo C Robert
*Assistant Examiner* — Michelle C Green
(74) *Attorney, Agent, or Firm* — Sheridan Ross P.C.

(57) ABSTRACT

A method for treating a spine, the method comprising the steps of: imaging a patient anatomy for registration of anatomical image data and positional tracking of the patient anatomy; selecting an implant strategy for at least one bone fastener; selecting a manipulation strategy for the patient anatomy; determining a post-correction orientation of the patient anatomy according to the implant strategy and the manipulation strategy; imaging the post-correction orientation of the patient anatomy; engaging the at least one bone fastener with vertebral tissue of the patient anatomy according to the implant strategy; and connecting a first implant support to the at least one bone fastener, the first implant support including an adaptor that is movable relative to the first implant support to releasably engage a surgical instru- (Continued)

ment to distract and/or compress the vertebral tissue according to the manipulation strategy. Surgical instruments, constructs and implants are disclosed.

20 Claims, 11 Drawing Sheets

(51) Int. Cl.
*A61B 17/88* (2006.01)
*A61B 34/10* (2016.01)
*A61B 17/02* (2006.01)
*A61B 17/56* (2006.01)
*A61B 34/20* (2016.01)
*A61B 90/00* (2016.01)

(52) U.S. Cl.
CPC ........ *A61B 17/864* (2013.01); *A61B 17/8811* (2013.01); *A61B 2017/0256* (2013.01); *A61B 2017/564* (2013.01); *A61B 17/708* (2013.01); *A61B 2034/104* (2016.02); *A61B 2034/107* (2016.02); *A61B 2034/2072* (2016.02); *A61B 2090/364* (2016.02)

(56) References Cited

U.S. PATENT DOCUMENTS

| | | |
|---|---|---|
| 8,974,497 B2 | 3/2015 | Cho et al. |
| 9,402,660 B2 | 8/2016 | Brinkman et al. |
| 10,314,620 B2 | 6/2019 | Cho et al. |
| 11,576,727 B2* | 2/2023 | Turner ................... A61B 34/10 |
| 12,114,845 B2 | 10/2024 | Josse et al. |
| 2006/0084844 A1 | 4/2006 | Nehls |
| 2007/0208227 A1 | 9/2007 | Smith et al. |
| 2008/0140129 A1 | 6/2008 | Dalton |
| 2010/0069976 A1 | 3/2010 | de Villiers et al. |
| 2012/0296172 A1 | 11/2012 | Raven, III et al. |
| 2012/0316609 A1 | 12/2012 | Wall et al. |
| 2013/0310942 A1 | 11/2013 | Abdou |
| 2014/0024900 A1 | 1/2014 | Capote et al. |
| 2014/0066718 A1 | 3/2014 | Fiechter et al. |
| 2014/0107656 A1 | 4/2014 | Masson et al. |
| 2014/0257044 A1 | 9/2014 | Blain et al. |
| 2014/0257312 A1 | 9/2014 | Solitario, Jr. et al. |
| 2014/0350347 A1 | 11/2014 | Karpowicz et al. |
| 2015/0045834 A1 | 2/2015 | McBride |
| 2015/0164569 A1 | 6/2015 | Reitblat et al. |
| 2015/0351738 A1 | 12/2015 | Perrow |
| 2016/0074029 A1 | 3/2016 | O'Connell et al. |
| 2016/0089188 A1 | 3/2016 | McBride, Jr. et al. |
| 2016/0166335 A1 | 6/2016 | Roger et al. |
| 2016/0206442 A1 | 7/2016 | Dvorak et al. |
| 2016/0345952 A1 | 12/2016 | Kucharzyk et al. |
| 2017/0035406 A1 | 2/2017 | Abidin et al. |
| 2017/0100116 A1 | 4/2017 | Erramilli et al. |
| 2017/0112539 A1 | 4/2017 | Hayes |
| 2017/0119449 A1 | 5/2017 | Jones et al. |
| 2017/0215856 A1 | 8/2017 | Martinelli et al. |
| 2017/0252107 A1 | 9/2017 | Turner et al. |
| 2017/0258502 A1 | 9/2017 | Abdou |
| 2017/0311985 A1 | 11/2017 | Bobbitt et al. |
| 2018/0042594 A1 | 2/2018 | Miles et al. |
| 2018/0161101 A1 | 6/2018 | Barsoum et al. |
| 2018/0289363 A1 | 10/2018 | Barnes et al. |
| 2018/0303473 A1 | 10/2018 | Spann et al. |
| 2018/0303552 A1 | 10/2018 | Ryan et al. |
| 2019/0021716 A1 | 1/2019 | Waugh et al. |
| 2019/0038366 A1 | 2/2019 | Johnson et al. |
| 2019/0046239 A1 | 2/2019 | Bobbitt et al. |
| 2019/0069956 A1* | 3/2019 | Ryan ..................... G16H 50/50 |
| 2019/0090864 A1 | 3/2019 | Medeiros et al. |
| 2019/0090979 A1 | 3/2019 | Medeiros et al. |
| 2019/0110785 A1 | 4/2019 | Serokosz et al. |
| 2019/0216453 A1 | 7/2019 | Predick et al. |
| 2019/0223854 A1 | 7/2019 | Baudouin et al. |
| 2020/0054361 A1 | 2/2020 | Peultier et al. |
| 2020/0085500 A1* | 3/2020 | Dace ..................... A61B 34/10 |
| 2022/0192645 A1 | 6/2022 | Peultier et al. |
| 2022/0202405 A1 | 6/2022 | Josse et al. |
| 2022/0202450 A1 | 6/2022 | Josse et al. |
| 2023/0059813 A1 | 2/2023 | Josse et al. |

FOREIGN PATENT DOCUMENTS

| | | | |
|---|---|---|---|
| CN | 110381866 | 10/2019 | |
| EP | 3331421 | 6/2018 | |
| EP | 3351185 | 7/2018 | |
| GB | 2528416 | 1/2016 | |
| KR | 10-1446620 B1 | 10/2014 | |
| WO | WO 90/02527 | 3/1990 | |
| WO | WO 2007/087536 | 8/2007 | |
| WO | 2018150214 A1 | 8/2018 | |
| WO | WO-2018150215 A1 * | 8/2018 | .......... A61B 17/708 |
| WO | WO 2020/219016 | 10/2020 | |
| WO | WO 2020/219018 | 10/2020 | |
| WO | WO 2020/219019 | 10/2020 | |
| WO | WO 2020/219020 | 10/2020 | |
| WO | WO 2021/206723 | 10/2020 | |

OTHER PUBLICATIONS

Official Action for U.S. Appl. No. 17/795,152, dated Nov. 26, 2024, 9 pages.
Notice of Allowance for U.S. Appl. No. 17/606,011, dated Dec. 5, 2024, 8 pages.
International Preliminary Report on Patentability for International (PCT) Patent Application No. PCT/US2019/028612, dated Sep. 28, 2021, 6 pages.
Extended European Search Report for Europe Patent Application No. 19925665.2, dated Nov. 4, 2022, 10 pages.
International Search Report and Written Opinion for International (PCT) Patent Application No. PCT/US2019/028615, dated Feb. 21, 2020, 8 pages.
International Preliminary Report on Patentability for International (PCT) Patent Application No. PCT/US2019/028615, dated Feb. 21, 2020, 7 pages.
Extended European Search Report for Europe Patent Application No. 19926119.9, dated Nov. 3, 2022, 9 pages.
Official Action for China Patent Application No. 201980095607.3, dated Jan. 25, 2024, 2 pages.
International Search Report and Written Opinion for International (PCT) Patent Application No. PCT/US2020/027533, dated Jul. 6, 2020, 8 pages.
International Preliminary Report on Patentability for International (PCT) Patent Application No. PCT/US2020/027533, dated Oct. 6, 2022, 7 pages.
Extended European Search Report for Europe Patent Application No. 20930065.6, dated Mar. 13, 2024, 5 pages.
International Search Report and Written Opinion for International (PCT) Patent Application No. PCT/US2019/028624, dated Feb. 21, 2020, 9 pages.
International Preliminary Report on Patentability for International (PCT) Patent Application No. PCT/US2019/028624, dated Sep. 28, 2021, 7 pages.
Extended European Search Report for Europe Patent Application No. 19925802.1, dated Nov. 8, 2022, 10 pages.
Official Action for Europe Patent Application No. 19925802.1, dated Jul. 18, 2024, 3 pages.
International Search Report and Written Opinion for International (PCT) Patent Application No. PCT/US2019/028628, dated Feb. 21, 2020, 7 pages.
International Preliminary Report on Patentability for International (PCT) Patent Application No. PCT/US2019/028628, dated Sep. 28, 2021, 6 pages.
Extended European Search Report for Europe Patent Application No. 19925884.9, dated Nov. 8, 2022, 11 pages.
Official Action for China Patent Application No. 201980095615.8, dated Jan. 23, 2024, 2 pages.

(56) References Cited

OTHER PUBLICATIONS

International Search Report and Written Opinion for International (PCT) Patent Application No. PCT/US2019/028632, dated Feb. 21, 2020, 7 pages.
International Preliminary Report on Patentability for International (PCT) Patent Application No. PCT/US2019/028632, dated Sep. 28, 2021, 6 pages.
Extended European Search Report for Europe Patent Application No. 19925589.4, dated Nov. 7, 2022, 12 pages.
Official Action for China Patent Application No. 201980095623.2, dated Jan. 23, 2024, 2 pages.
Official Action for U.S. Appl. No. 17/605,819, dated Feb. 15, 2024, 10 pages.
Official Action for U.S. Appl. No. 17/605,819, dated Jul. 22, 2024, 12 pages.
Official Action for U.S. Appl. No. 17/605,819, dated Sep. 27, 2024, 13 pages.
Official Action for U.S. Appl. No. 17/606,010, dated Dec. 20, 2023, 16 pages.
Notice of Allowance for U.S. Appl. No. 17/606,010, dated Jul. 9, 2024, 5 pages.
Corrected Notice of Allowance for U.S. Appl. No. 17/606,010, dated Jul. 29, 2024, 2 pages.
Notice of Allowance for U.S. Appl. No. 17/606,010, dated Sep. 16, 2024, 5 pages.
Official Action for U.S. Appl. No. 17/606,011, dated Jan. 18, 2024, 9 pages.
Official Action for U.S. Appl. No. 17/606,011, dated Jul. 3, 2024, 11 pages.
Official Action for U.S. Appl. No. 17/606,013, dated Sep. 15, 2023, 5 pages. Restriction Requirement.
Official Action for U.S. Appl. No. 17/606,013, dated Mar. 21, 2024, 25 pages.
Official Action for U.S. Appl. No. 17/606,013, dated Jun. 12, 2024, 26 pages.
European Patent Office, 80298 Munich, Germany, Application No. 19925665.2, Extended European Search Report, Date Apr. 11, 2022.
International Search Report for PCT/US2019/028612 date of completion is Feb. 21, 2020 (2 pages).
Article 94(3) Communication for Europe Patent Application No. 19925665.2, dated Dec. 17, 2024, 8 pages.
Notice of Allowance for U.S. Appl. No. 17/795,152, dated Mar. 12, 2025, 8 pages.
Notice of Allowance for U.S. Appl. No. 17/606,013, dated Mar. 13, 2025, 8 pages.
Notice of Allowance for U.S. Appl. No. 17/605,819, dated Jan. 23, 2025, 8 pages.

* cited by examiner

SURGICAL SYSTEM AND METHOD

CROSS-REFERENCE TO RELATED APPLICATIONS

This application is a National Stage Application of PCT/US2019/028612 filed Apr. 23, 2019, and the disclosure of the above-identified application is hereby incorporated by reference in its entirety.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, scoliosis, kyphosis, and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In one embodiment, a method for treating a spine is disclosed. The method comprises the steps of: imaging a patient anatomy for registration of anatomical image data and positional tracking of the patient anatomy; selecting an implant strategy for at least one bone fastener; selecting a manipulation strategy for the patient anatomy; determining a post-correction orientation of the patient anatomy according to the implant strategy and the manipulation strategy; imaging the post-correction orientation of the patient anatomy; engaging the at least one bone fastener with vertebral tissue of the patient anatomy according to the implant strategy; and connecting a first implant support to the at least one bone fastener, the first implant support including an adaptor that is movable relative to the first implant support to releasably engage a surgical instrument to distract and/or compress the vertebral tissue according to the manipulation strategy. In some embodiments, surgical systems, instruments, constructs and implants are disclosed.

In one embodiment, the method for treating a spine comprises the steps of: attaching a reference marker to the patient anatomy; imaging a patient anatomy for registration of anatomical image data and positional tracking of the patient anatomy; selecting an implant strategy for at least one bone fastener; selecting a manipulation strategy for the patient anatomy; determining a post-correction orientation of the patient anatomy according to the implant strategy and the manipulation strategy; imaging the post-correction orientation of the patient anatomy; connecting the at least one bone fastener with a surgical driver having a navigation component and engaging the at least one bone fastener with vertebral tissue of the patient anatomy according to the implant strategy; injecting cement through the at least one bone fastener into a vertebra of the patient anatomy; connecting a first implant support to the at least one bone fastener, the first implant support including an adaptor that is movable relative to the first implant support to releasably engage a surgical instrument to distract and/or compress the vertebral tissue according to the manipulation strategy; and comparing an actual correction orientation of the patient anatomy according to the manipulation strategy with the determined post-correction orientation.

In one embodiment, a surgical system is provided. The surgical system comprises at least one implant support includes a first implant support that is engageable with a receiver of a first fastener having a shaft fixed with vertebral tissue. The receiver includes at least one tab extender. The shaft includes a proximal portion and a closed distal tip. The shaft further includes an outer surface engageable with a first cortical surface and a second cortical surface. The proximal portion includes an inner surface that defines a longitudinal cavity and at least one fenestration in communication therewith. The first implant support includes a connector releasably engageable with the at least one tab extender. The first implant support further includes an adaptor. At least a portion of the adaptor is movable relative to the first implant support to releasably engage a surgical instrument to distract and/or compress the vertebral tissue. An image guide is oriented relative to a sensor for registration of anatomical image data and positional tracking of the patient anatomy.

BRIEF DESCRIPTION OF THE DRAWINGS

The present disclosure will become more readily apparent from the specific description accompanied by the following drawings, in which.

DETAILED DESCRIPTION

Figure 1:
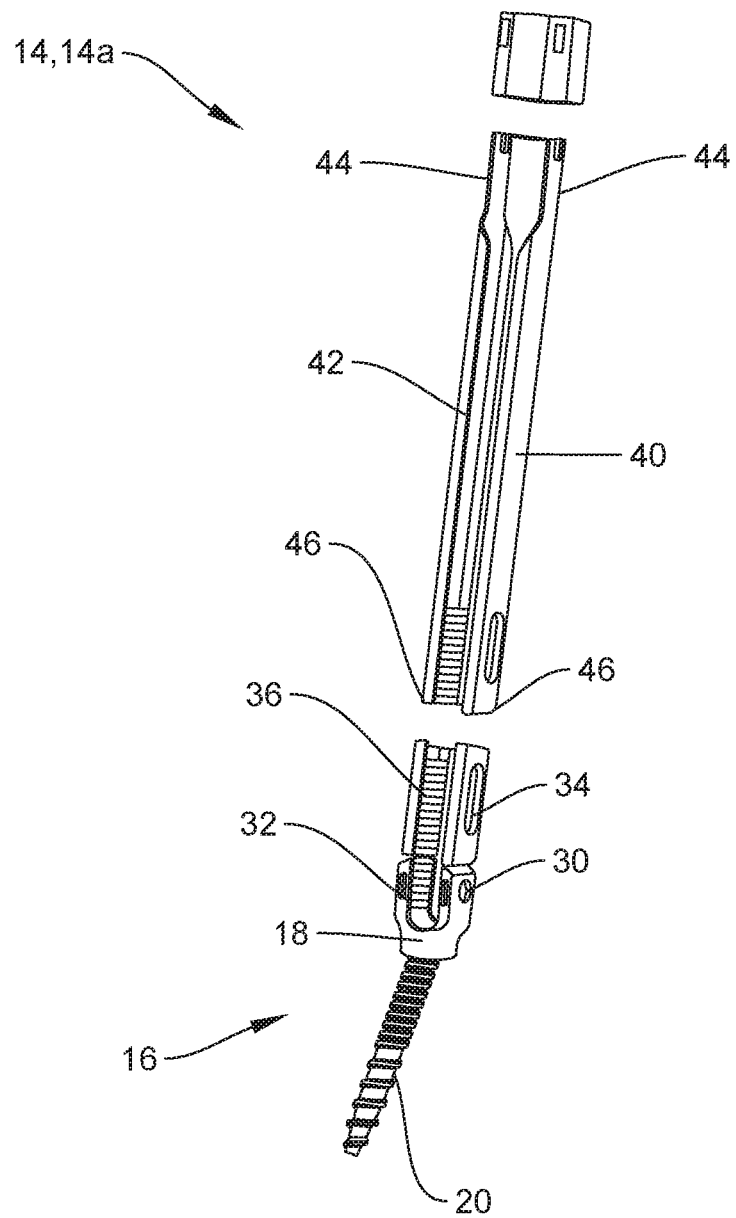
FIG. 1 is a perspective view of components of one embodiment of a surgical system in accordance with the principles of the present disclosure disposed with vertebrae.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system includes one or more surgical instruments that allow vertebral manipulation to treat spinal disorders, as described herein, for managing lordosis and/or kyphosis restoration. In some embodiments, the present surgical system includes one or more surgical instruments that allow for parallel distraction and/or compression of vertebral tissue.

In some embodiments, the present surgical system can be employed with fracture reduction. In some embodiments, the present surgical system includes a fracture reduction system that employs surgical navigation and instrumentation to provide measurement capability. In some embodiments, the instrumentation includes fenestrated bone screws, for example, cement-augmented screws. In some embodiments, the fracture reduction system allows restoration of an angle during ligamentotaxy at a level of an implant, such as, for example, a head of a screw disposed at a surgical site to facilitate a more precise reduction of the trauma. In some embodiments, the fracture reduction system facilitates burst fracture reduction and/or deformity correction procedures. In some embodiment, to treat burst fractures, the fracture reduction system utilizes fenestrated bone screws including a sagittal adjusting screw (SAS), a fixed angle screw (FAS) and/or a multi-axial screw (MAS) for treating tumor, trauma and/or deformity disorders with instrumentation.

In some embodiments, the present surgical system includes a cement delivery system for fenestrated screws before and after a selected manipulation strategy including a procedure for correction. In some embodiments, the present surgical system includes a multi-level percutaneous fixation system and other features such as integrated extensions, and a low profile configuration. In some embodiments, the present surgical system includes a cement delivery system that delivers cement and/or other materials to one or more fenestrated screws to achieve various desired characteristics such as strength, rigidity, elasticity, compliance, biomechanical performance, durability and radiolucency or imaging preference on the implanted screws. In some embodiments, the present surgical system includes measurement capability that allows measurement and calculation of screw positions, relative correction and/or geometric parameters associated with the implanted screws. In some embodiments, the measurement capability is enabled by a computer through navigation software to quantify ligamentotaxy or kyphosis correction. In some embodiments, the present surgical system includes measurement capability that facilitates navigation of screws during a surgical procedure, which minimizes the exposure to radiation or other radioactive scanning devices.

In some embodiments, the present surgical system can be employed with a fracture reduction method including the steps of attaching a navigation reference marker with a patient anatomy, imaging the patient anatomy for registration of anatomical image data and positional tracking of the patient anatomy, implanting screws with driver that has a navigation component attached, imaging screws and vertebrae with a driver having a navigation component such that the navigation system projects and/or reproduces an image of the implant disposed with vertebrae on a computer screen. The image may include pre and post-correction orientation of the patient anatomy. In some embodiments, the method further includes the steps of selecting an implant strategy for at least one bone fastener; selecting a manipulation strategy for the patient anatomy prior or post the correction of vertebrae or other surgical process performed; a computer calculating a preferred correction based on screw orientation with vertebrae-pre correction; attaching a distractor to screws and/or employ other surgical instruments, selectively injecting cement with fractured vertebrae with a tool through fenestrated screws; performing correction with the distractor; imaging screws with vertebrae-post correction, comparing and/or evaluating calculated correction with actual correction on the navigation system.

In some embodiments, the present surgical system includes a surgical trauma instrument. In some embodiments, the present surgical system is utilized with a method to correct complex spinal deformities. In some embodiments, the present surgical system is utilized with a method to treat degenerative spinal disorders and/or employed with transforaminal lumbar interbody fusion procedures. In some embodiments, the present surgical system comprises a plurality of compressor/distractors, such as, for example, two distractors disposed along a side of vertebrae to perform a ligamentotaxy procedure. In some embodiments, the present surgical system comprises a single distractor to treat degenerative spinal disorders, for example, for disposal along a side of vertebrae oriented for decompression and/or interbody cage insertion.

In some embodiments, the present surgical system includes a percutaneous surgical system for use in a ligamentotaxy of a traumatic thoracic lumbar spine. In some embodiments, the present surgical system includes a surgical system that allows restoration of an angle during ligamentotaxy at a level of an implant, such as, for example, a head of a screw disposed at a surgical site to facilitate a more precise reduction of the trauma.

In some embodiments, the present surgical system includes a surgical instrument connected with an adaptor, which is utilized with a bone screw having extender tabs attached thereto. In some embodiments, the present surgical system includes an implant support including a connector and an adaptor. In some embodiments, the connector includes an outer sleeve configured for connection with extenders. In some embodiments, the connector is connected with extenders for insertion of an implant, such as for example, a spinal rod. In some embodiments, the adaptor includes an arm having a pivot hinge that connects the connector with a compressor/retractor. In some embodiments, the pivot hinge allows movement of the components to provide surgical-site visibility for inter-operative imaging. In some embodiments, a compressor/distractor is utilized for parallel distraction. In some embodiments, the surgical instrument includes a compressor/distractor having a reversible ratchet with a neutral, freely moveable position. In some embodiments, the present surgical system is employed with a procedure for implantation of a bone fastener percutaneously.

In some embodiments, the present surgical system includes a surgical instrument configured to compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, degenerative kyphosis. In some embodiments, the present surgical system is employed to treat hyper-kyphosis, flat lumbar back, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

In some embodiments, one or all of the components of the surgical system are disposable, peel-pack, pre-packed sterile devices used with a spinal construct. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis, kyphosis, and other curvature abnormalities, tumor and fractures. In some embodiments, the present disclosure may be employed with other osteo and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including posterior and/or posterior mid-line and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
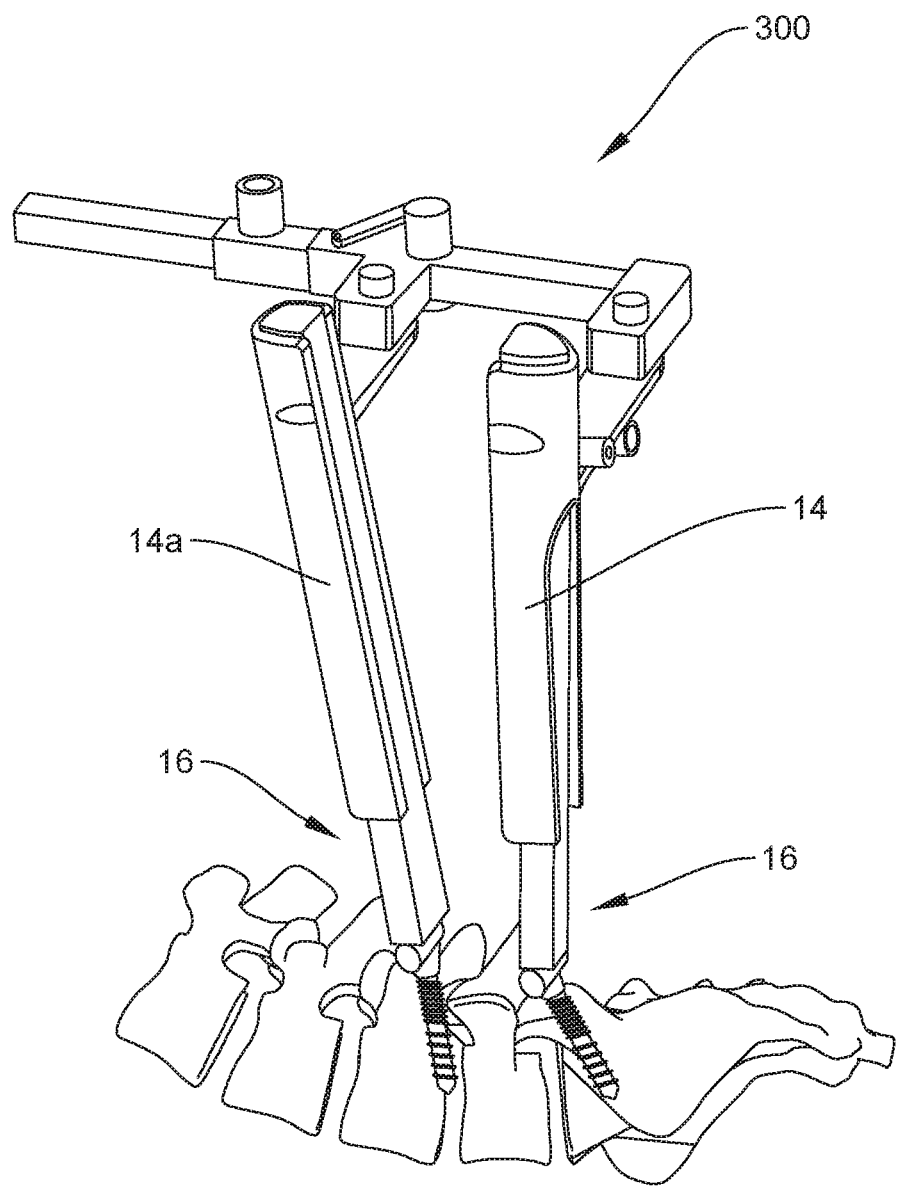
FIG. 2 is a perspective view of components of one embodiment of a surgical system in accordance with the principles of the present disclosure disposed with vertebrae.
Figure 3:
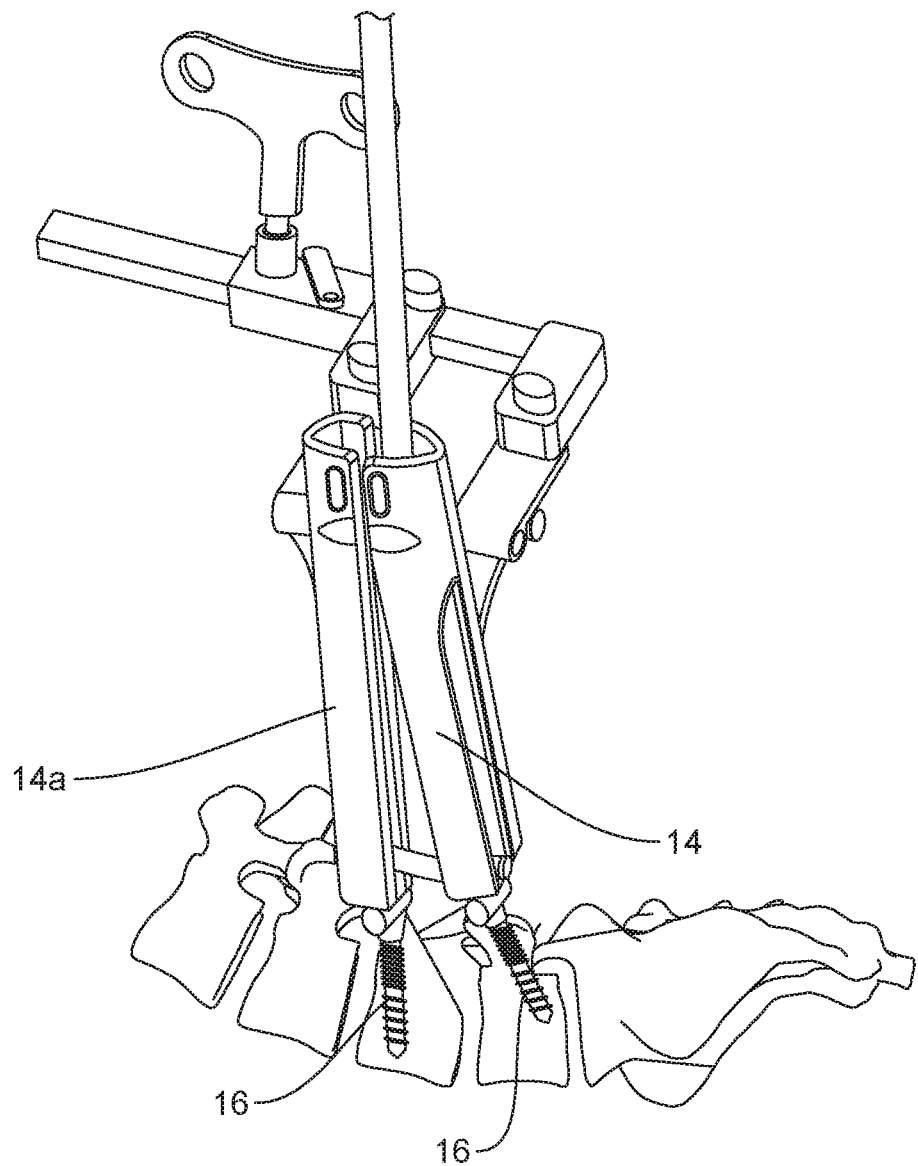
FIG. 3 is a perspective view of components, disposed with vertebrae, of one embodiment of a surgical system in accordance with the principles of the present disclosure.

The following discussion includes a description of a surgical system and related methods of employing the surgical system in accordance with the principles of the present disclosure. Alternate embodiments are disclosed. Reference is made to the exemplary embodiments of the present disclosure, which are illustrated in the accompanying figures. Turning to FIGS. 1-3, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of surgical system 10 are configured for engagement with spinal constructs attached with vertebrae to manipulate tissue and/or correct a spinal disorder, such as, for example, a sagittal deformity, as described herein. In some embodiments, surgical system 10 may be employed with surgical procedures, such as, for example, corpectomy, discectomy and/or fracture/trauma treatment and may include fusion and/or fixation that employ implants to restore the mechanical support function of vertebrae.

Surgical system 10 includes a surgical instrument, such as, for example, an implant support 14 and an implant support 14a, similar to implant support 14, as show in FIG. 2. Implant supports 14, 14a are each connectable with a bone fastener 16 having a receiver 18 and a screw shaft 20, as shown in FIGS. 1-3. Screw shaft 20 is fixed with tissue. Receiver 18 is connectable with implant support 14 to releasably engage a surgical instrument, such as, for example, a compressor/distractor 300 to distract and/or compress tissue.

Receiver 18 includes a pair of spaced apart arms 30, 32 that define an implant cavity configured for disposal of a component of a spinal construct, such as, for example, a spinal rod. Receiver 18 includes an inner surface having a thread form located disposed with arms, 30, 32. Screw shaft 20 is configured to penetrate tissue, such as, for example, bone, of a patient.

Arm 30 includes a break away tab 34 that is frangibly connected to arm 30 such that manipulation of tab 34 relative to arm 30 can fracture and separate tab 34 from arm 30 at a predetermined force and/or torque limit. Arm 32 includes a break away tab 36 that is frangibly connected to arm 32 such that manipulation of tab 36 relative to arm 32 can fracture and separate tab 36 from arm 32 at a predetermined force and/or torque limit, as described herein. In some embodiments, as force and/or torque is applied to tabs 34, 36 and resistance increases, for example, the predetermined torque and force limit is approached.

Implant support 14 includes extender tabs 40, 42 that are connectable with bone fastener 16, as shown in FIG. 1. Each extender tab 40, 42 extends between a proximal end 44 and a distal end 46. Distal ends 46 are configured for slidable disposal of a portion of bone fastener 16, such as, for example, tabs 34, 36. In some embodiments, tabs 34, 36 are configured to releasably fix extender tabs 40, 42 with bone fastener 16 for connection with implant support 14, as described herein. In some embodiments, bone fastener 16 includes at least one extender tab. For embodiments lacking tabs 34, 36, the extender tabs 40, 42 can connect directly to the arms 30, 32.

In some embodiments, connection of implant supports 14, 14a facilitates correction of a vertebral angle of vertebrae, for example, to achieve a selected lordosis and/or kyphosis, via manipulation of implant supports 14, 14a, as described herein. In some embodiments, implant supports 14, 14a are connected with compressor/distractor 300 to maintain a corrected vertebral angle of vertebrae during distraction and/or compression, as described herein. In some embodiments, the compressor/distractor has direct connection to extender (top-loading) and the screws such that the system provides direct control ligamentotaxy/kyphosis correction and at a reduced profile. In some embodiments, the present surgical system also provides ergonomic instrumentation that connects the implant, implant support and other rack and lordosis module assembly. In some embodiments, the present surgical system is configured for open and/or mini-open approach and configured as a pre-assembled single block top loading. In some embodiments, the surgical system includes an angulation module to facilitate compression/distraction. In some embodiments, an angulation module is configured for connection with the extenders 40, 42. For example, an angulation module may move the extenders close together in a compression process as shown in FIG. 3. In some embodiments, the angulation module is monolithic with the at least one implant support 14.

In assembly, operation and use, surgical system 10, similar to the systems and methods described herein, is employed with a surgical procedure, for treatment of a spine of a patient including vertebrae V. Surgical system 10 may also be employed with surgical procedures, such as, for example, discectomy, lam inectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 4:
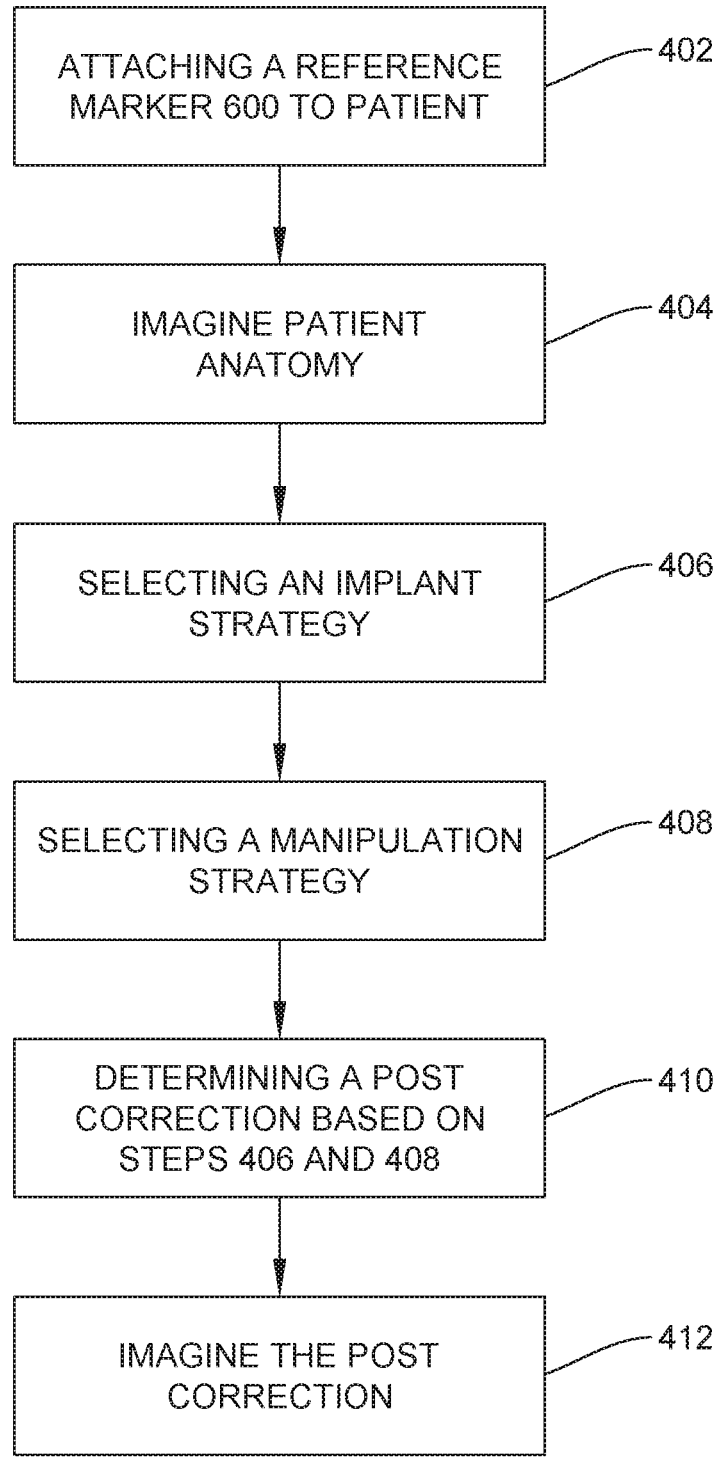
FIGS. 4 and 5 are flow diagrams illustrating representative steps of embodiments of a method and a surgical system in accordance with the principles of the present disclosure.
Figure 5:
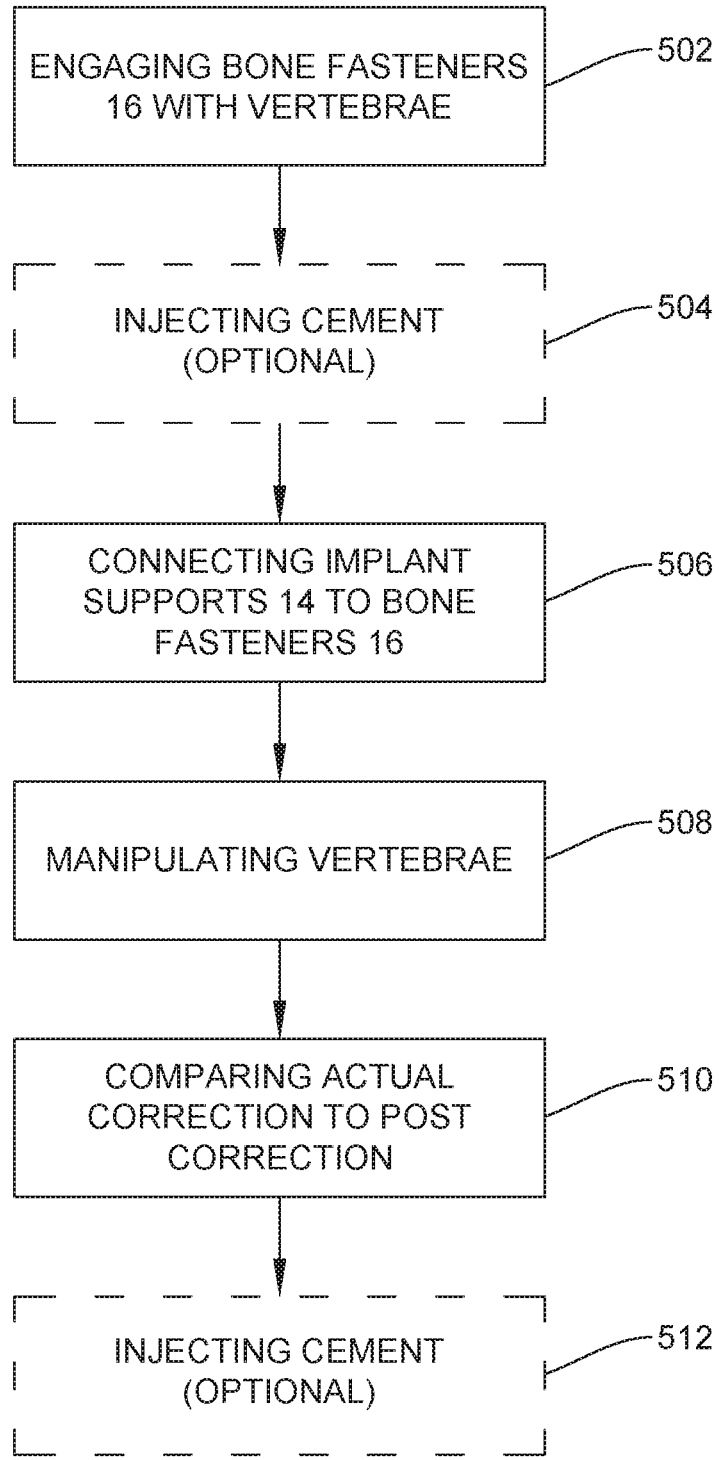

In various embodiment, as shown by way of examples in FIGS. 4-12, spinal implant system 10, similar to the systems and methods described herein, is employed in connection with one or more surgical procedures, as described herein. Initially, spinal implant system 10 is employed with a method for treating a spine that includes a preparation and/or a pre-operative procedure 400, as shown in FIG. 4. Surgical method 500, as shown in FIG. 5, includes use of components and/or surgical instruments for delivery of components of spinal implant system 10, which, such as, for example, drivers, extenders, reducers, spreaders, distractors, blades, clamps, forceps, elevators and drills, any of which may be alternately sized and dimensioned, and any of which may be arranged as a kit.

Figure 6:
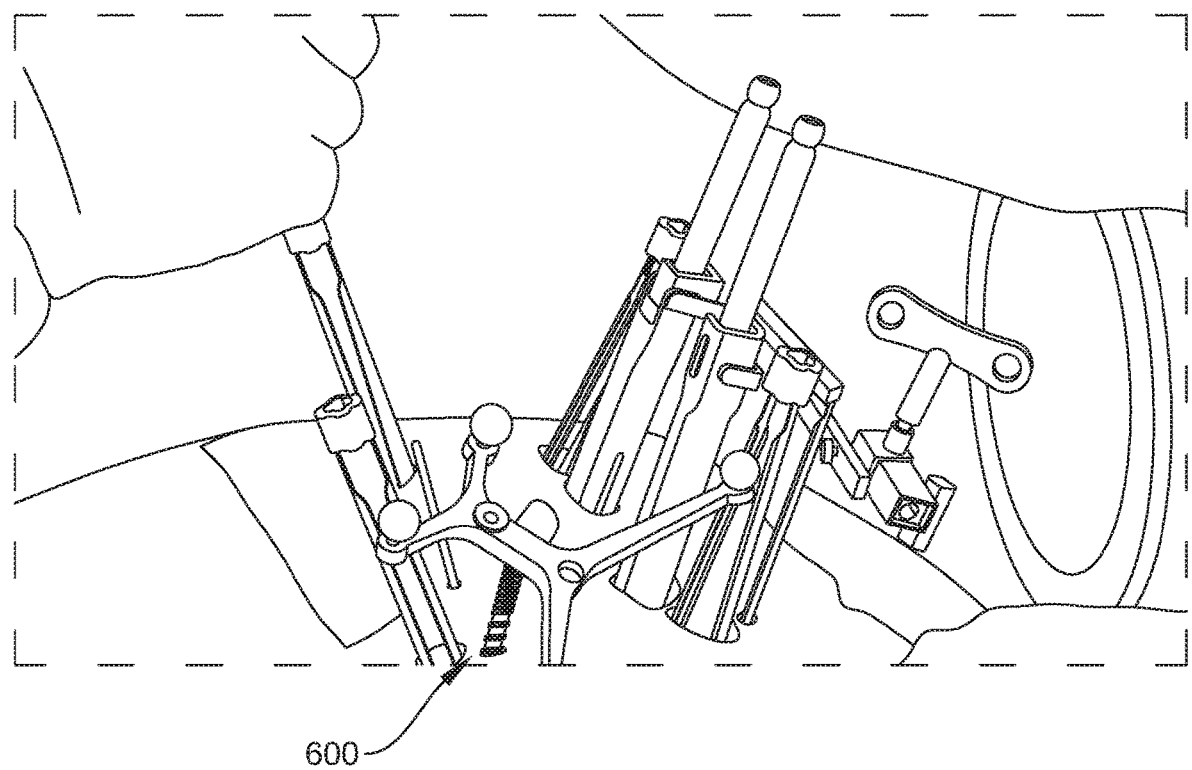
FIG. 6 is a perspective view of components of one embodiment of a surgical system in accordance with the principles of the present disclosure disposed with vertebrae.

In preparation and/or a pre-operative procedure 400, step 402 includes attaching a 3D reference marker 600, as shown in FIG. 6, to the patient. Marker 600 is visible by surgical navigation system 216, shown in FIGS. 8 and 9. Marker 600 is utilized to obtain images bone fastener 16 in a coronal, cephalad and/or caudal space during angulation, distraction and/or derotation. In some embodiments, markers 600 can be utilized with two or a plurality of bone fasteners 16 at multiple vertebral levels. For example, prior to manipulation of the vertebral segment, a machine can overlay bone fasteners 16 to vertebrae V.

Step 404 includes imaging vertebrae V for registration of anatomical image data and positional tracking of vertebrae V, for example, a CT scan or MRI scan. In some embodiments, the images include taking C-arm images of the patient anatomy. The images are calibrated such that a three-dimensional image of the selected vertebrae is generated. In some embodiments, fluoroscopic images are taken from different angles, such as, 0, 45, and 90 degrees. In some embodiments, multiple C-arm images are taken. For example, step 404 may include imaging the vertebrae V by performing a three-dimensional scan of the selected vertebrae V. In some embodiments, step 404 includes utilizing O-Arm® imaging device in the operating room to obtain the three-dimensional images of the patient anatomy intra-operatively and/or prior to surgery 500 for calibration and registration.

During a registration process, the three-dimensional scans from step 404 are transferred to a control unit. See, for example, the registration systems and methods, as described in U.S. Pat. No. 8,571,638, the contents of which being hereby incorporated by reference herein in its entirety. The C-arm images from step 404 are transferred to the control unit. A pseudo three-dimensional image of the selected vertebrae V is generated for patient anatomy registration, FIG. 8. For example, at pre-correction, the relative angle between a first bone fastener 16 is about 51 degrees relative to a second bone fastener 16 and a distance is about 41 mm.

In step 406, a surgeon reviews three-dimensional the images captured in step 404 and formulates and selects an implant strategy according to three-dimensional scans.

Figure 7:
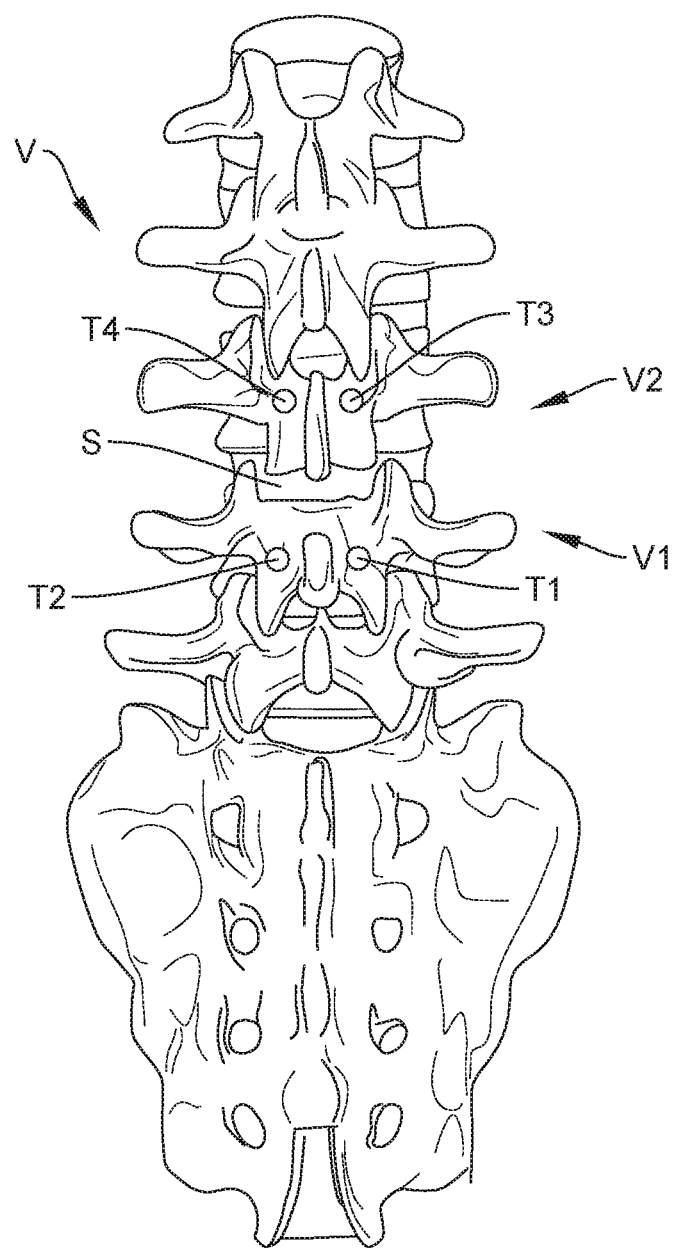
FIG. 7 is a plan view of one embodiment of an implant strategy in accordance with the principles of the present disclosure.
Figure 8:
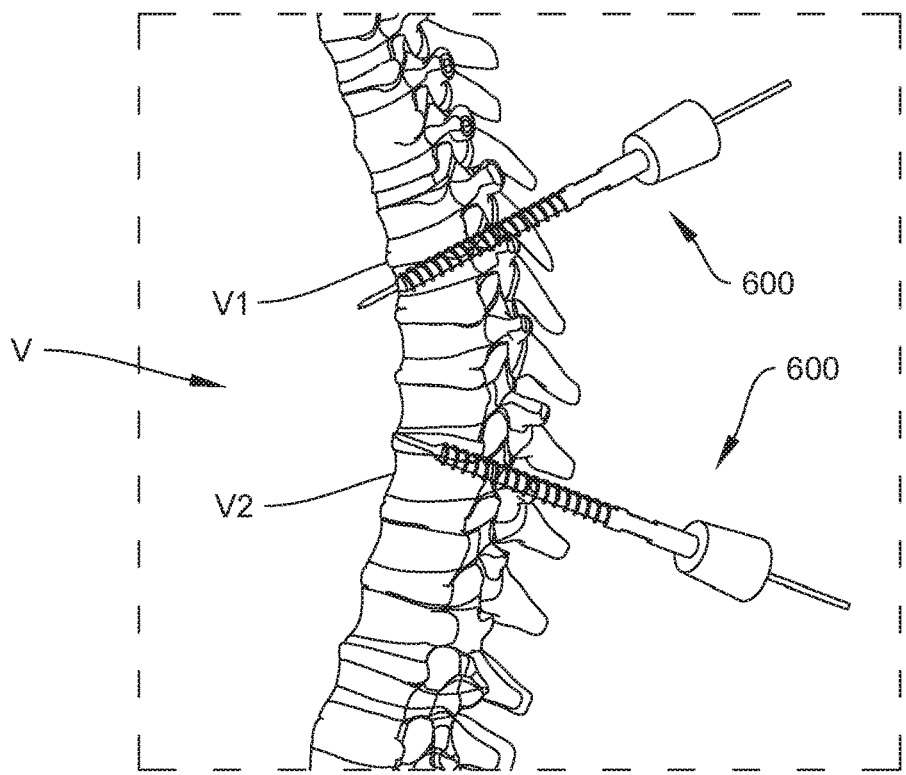
FIGS. 8 and 9 are graphical representations of a computer showing components of one embodiment of a spinal implant system in accordance with the principles of the present disclosure.

Step 406 includes selecting an implant strategy for bone fasteners 16. For example, step 406 includes selecting a plurality of trajectories, such as, for example, trajectories T1, T2, T3 and T4 for bone fasteners 16 for positioning and engaging with vertebrae V, as shown in FIG. 7. In some embodiments, step 406 utilizes pre-operative analytics software including anatomy recognition and vertebral segmentation algorithms for surgical visualization based on a patient's images, which facilitates formulating the implant strategy including implant and trajectory placement planning.

Step 408 includes selecting a manipulation strategy for bone fasteners 16. Step 408 includes forming a strategy for manipulating a first bone fastener 16 a selected angular orientation relative to a second bone fastener 16 to decompress the vertebral tissue of vertebrae V1, V2.

Step 410 includes determining a post-correction orientation of vertebrae V1, V2 according to the implant strategy from step 406 and the manipulation strategy from step 408. In various embodiments, step 410 includes calculating or otherwise determining the post-correction orientation using a specially configured computing system having a processor. In various embodiments, calculating the post-correction orientation is done by a specially configured computing device (e.g., a processor executing software customized for the present purpose).

Figure 9:
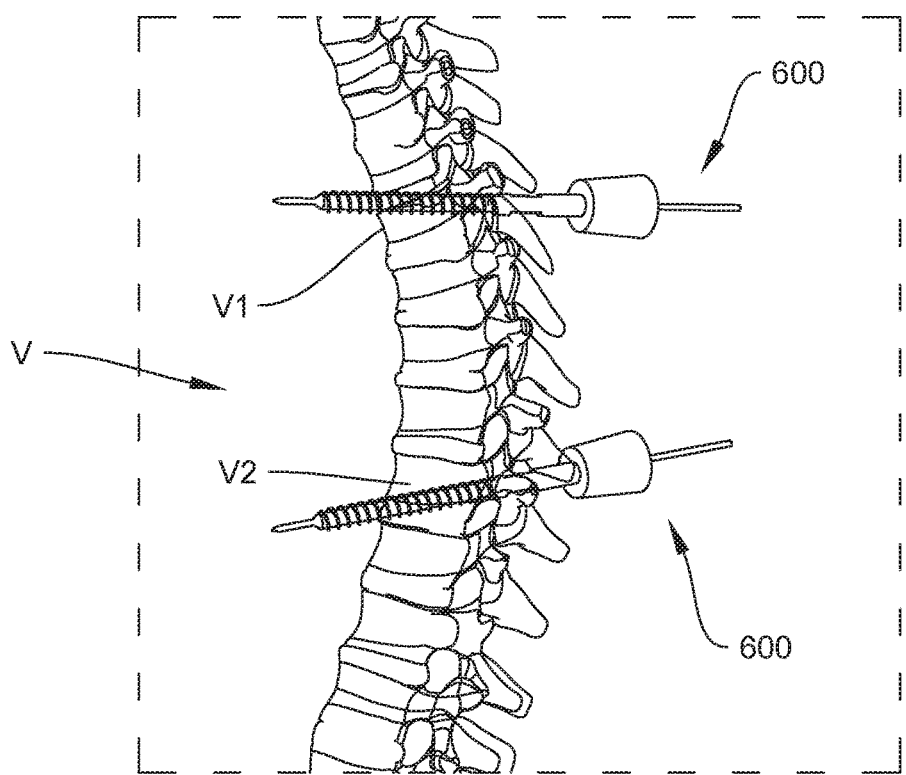

Step 412 includes imaging the calculated post-correction orientation, as shown in FIG. 9. For example, the calculated post correction would manipulate bone fasteners 16 such that the relative angle between the first bone fastener 16 is about 7 degrees relative to the second bone fastener 16 and a distance is about 27 mm.

In contemplated embodiments, any of the steps of the methods described herein can be performed by a specially configured computing system—e.g., a processor executing instructions, stored on a tangible, non-transitory, computer-readable storage device, customized for the present purpose.

Figure 10:
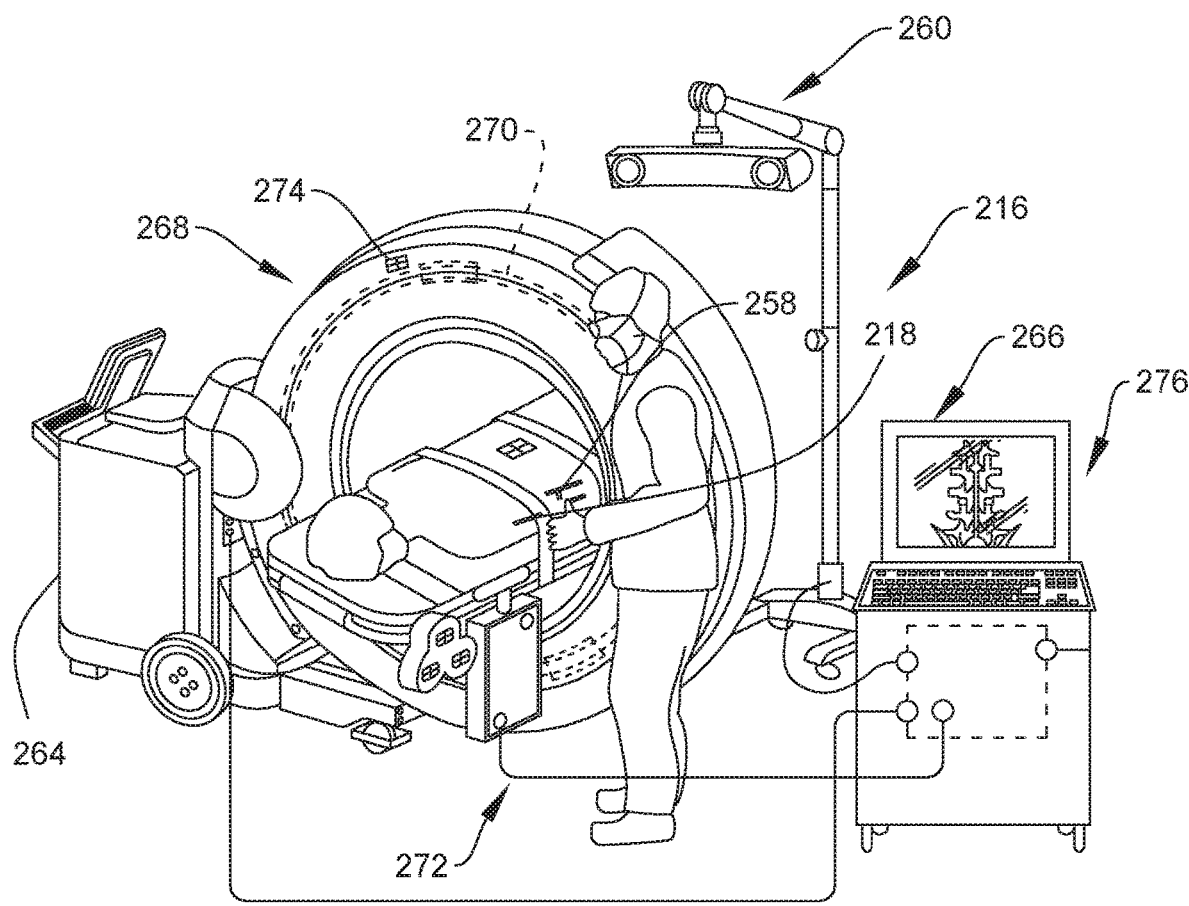
FIG. 10 is a perspective view of one embodiment of a manipulation strategy in accordance with the principles of the present disclosure.

During surgery 500, step 502 includes engaging bone fasteners 16 with vertebrae V1, V2 (see e.g., FIGS. 8 and 9) along trajectories T1, T2, T3 and T4 (see e.g., FIG. 7) according to the implant strategy developed in step 406. Bone fasteners 16 are connected with a surgical instrument, such as, for example, a driver 218 including a navigation component 258, as shown in FIG. 10. Navigation component 258 generates a signal representative of a position of each bone fastener 16 relative to vertebrae V1, V3 based on the actual correction orientation.

Navigation component 258 transmits a signal and communicates with a processor of computer 264 of a navigation system 216, as shown in FIG. 10. In various embodiments, navigation component 258 includes an emitter array. The emitter array is configured for generating a signal to a sensor array 260 of surgical navigation system 16. In some embodiments, the signal generated by emitter array 262 represents a position of bone fastener 16 relative to driver 218 and relative to tissue, such as, for example, bone. In some embodiments, the signal generated by emitter array 262 represents a three-dimensional position of bone fastener 16 relative to tissue.

In some embodiments, sensor array 260 receives signals from emitter array 262 to provide a three-dimensional spatial position and/or a trajectory of bone fastener 16 relative to driver 218 and/or tissue. Emitter array 262 communicates with a processor of computer 264 of navigation system 216 to generate data for display of an image on a monitor 266. In some embodiments, sensor array 260 receives signals from emitter array 262 to provide a visual representation of a position of bone fastener 16 relative to driver 218 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 216 is configured for acquiring and displaying medical imaging, such as, for example, x-ray images appropriate for a given surgical procedure. In some embodiments, pre-acquired images of a patient are collected. In some embodiments, surgical navigation system 216 can include an O-arm® imaging device 268 sold by Medtronic Navigation, Inc., having a place of business in Louisville, Colo., USA. Imaging device 68 may have a generally annular gantry housing that encloses an image capturing portion 270.

In some embodiments, image capturing portion 270 includes an x-ray source or emission portion and an x-ray-receiving, or other image-receiving, portion located generally, or as practically possible, 180 degrees from each other and mounted on a rotor (not shown in detail) relative to a track of image-capturing portion 270. Image-capturing portion 270 can be operable to rotate 360 degrees during image acquisition. Image-capturing portion 270 may rotate around a central point or axis, allowing image data of the patient to be acquired from multiple directions or in multiple planes. Surgical navigation system 216 can include those disclosed in U.S. Pat. Nos. 8,842,893, 7,188,998; 7,108,421; 7,106, 825; 7,001,045; and 6,940,941; the entire contents of each of these references being incorporated by reference herein.

The images, e.g., fluoroscopic images, taken are transmitted to computer 264, which may further forward them toto a computer 276. Image transfer may be performed using any channel, wireless or wired, such as over a standard video connection or a digital link including wired and wireless. In various embodiments, computer 276 provides the ability to display, via monitor 266, as well as save, digitally manipulate, or print a hard copy of the received images. In some embodiments, images may also be displayed to the surgeon through a heads-up display. In a contemplated embodiment, one computer is employed, here, instead of the two computers 264, 276.

Figure 11:
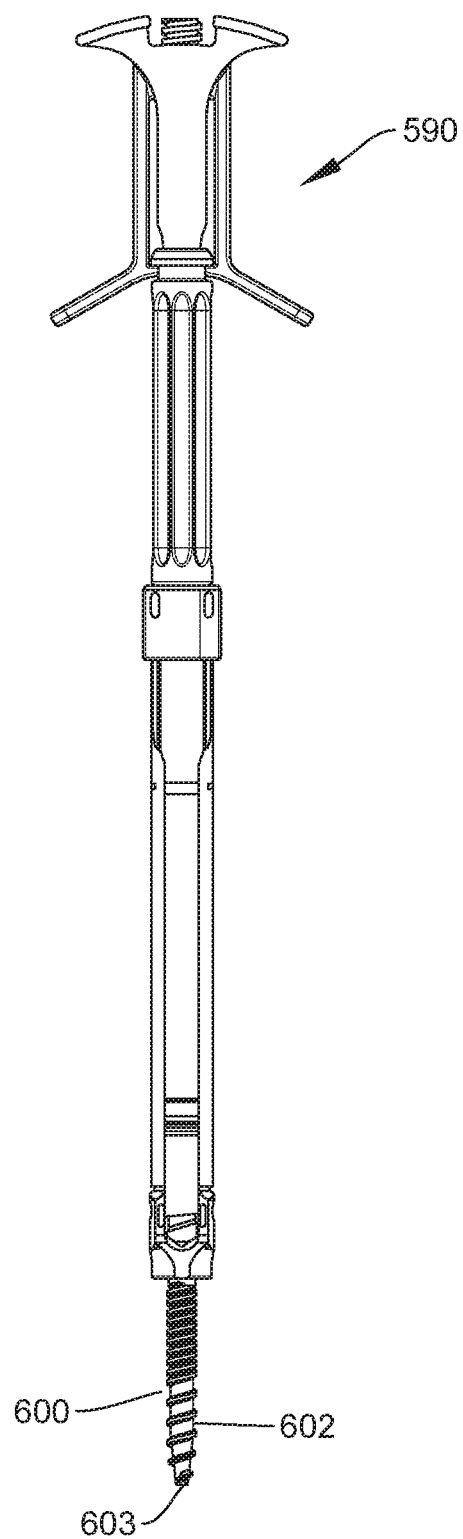
FIG. 11 is a side view of one embodiment of a manipulation strategy in accordance with the principles of the present disclosure.
Figure 12:
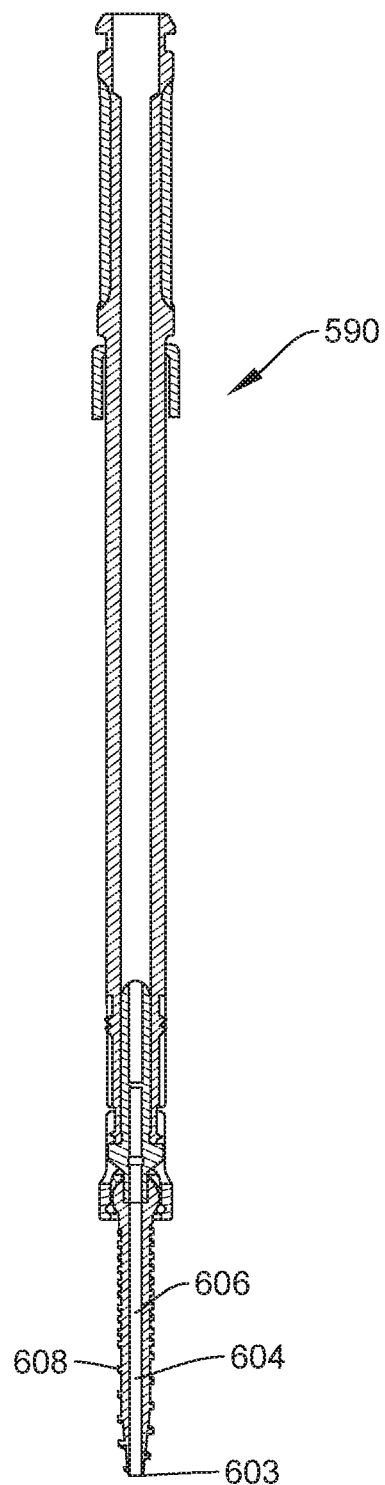
FIG. 12 is a side view of one embodiment of a manipulation strategy in accordance with the principles of the present disclosure.

In some embodiments, in step 504 a surgical instrument, such as, for example, a cement delivery device 590, as shown in FIGS. 11 and 12, is connected with bone fasteners 16 to inject cement through bone fasteners 16 into vertebrae V1, V2. In some embodiments, bone fasteners 16 includes fenestrated bone fasteners 160, as shown in FIGS. 11 and 12. In some embodiments, bone fastener 600 includes a shaft 602 including a proximal portion and a closed distal tip 603. Shaft 602 includes an outer surface engageable with a first cortical surface and a second cortical surface of bone. The proximal portion includes an inner surface 604 that defines a longitudinal cavity 606. Shaft 602 includes at least one opening, such as, for example, a fenestration 608 in communication with cavity 606 for dispersing the cement into vertebrae V. In some embodiments, bone fasteners 16 include sagittally adjustable screws. The bone fasteners 16 can in any way be like those described in U.S. patent Ser. No. 16/047,590, which is in its entirety incorporated herein.

In step 506 implant supports 14, 14a are connected with bone fasteners 16. For example, implant supports 14, 14a are connected with extenders 40, 42, as described herein.

In step 508, compressor/distractor 300 is mounted with adaptors 100, as described herein, to allow for manipulation via distraction and/or compression of vertebrae V1, V2 for the actual correction based on the manipulation strategy developed at step 408.

Step 510 includes comparing the actual correction from step 508 of vertebrae V1, V2 with the post-correction determined in steps 410 and 412.

In some embodiments, in step 512, cement delivery device 590 is connected with bone fasteners 160, as described herein, to inject cement through bone fasteners 160 into vertebral space S of vertebrae V1, V2.

Upon completion of one or more surgical procedures, the surgical instruments and non-implanted components of spinal implant system 10 are removed and the incision(s) are closed. One or more of the components of spinal implant system 10 can be made of radiolucent materials such as polymers. In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine, comprising:
    imaging a patient anatomy for registration of anatomical image data and positional tracking of the patient anatomy;
    determining an implant strategy for at least two bone fasteners, each one of the at least two bone fasteners comprising a reference marker trackable in a 3D space;
    determining, based on the patient anatomy and the implant strategy, a manipulation strategy;
    determining a post-correction orientation of the patient anatomy according to the implant strategy and the manipulation strategy;
    imaging the post-correction orientation of the patient anatomy;
    engaging each of the at least two bone fasteners to vertebral tissue of the patient anatomy according to the implant strategy;
    each of the at least two bone fasteners engageable with a surgical driver comprising a navigation component structured to generate a signal representative of a 3D spatial position of each of the reference markers of the at least two bone fasteners relative to the surgical driver;
    connecting a first implant support to a first of the at least two bone fasteners, the first implant support including an adaptor that is movable relative to the first implant support to releasably engage a surgical instrument to distract and/or compress the vertebral tissue according to the manipulation strategy, and
    the manipulation strategy comprising manipulating at least the first of the at least two bone fasteners a selected distance relative to a second of the at least two bone fasteners.

2. A method as recited in claim 1, wherein imaging the patient anatomy includes performing a three-dimensional scan of selected vertebrae of the patient anatomy.

3. A method as recited in claim 1, wherein selecting the implant strategy includes selecting a screw trajectory for a screw shaft of each one of the two bone fasteners connecting the screw shaft to the vertebral tissue.

4. A method as recited in claim 1, wherein the at least two bone fastener includes a plurality of pedicle screws and the implant strategy includes a corresponding plurality of respective screw trajectories for positioning the screws with a first vertebra and a second vertebra of the patient anatomy.

5. A method as recited in claim 1, wherein the at least two bone fasteners include a first bone screw disposed with a first vertebra of the patient anatomy and a second bone screw disposed with a second vertebra of the patient anatomy, and the manipulation strategy includes manipulating the first bone screw a selected angular orientation relative to the second bone screw.

6. A method as recited in claim 1, further comprising comparing an actual correction orientation of the patient anatomy, the manipulation strategy, with the determined post-correction orientation.

7. A method as recited in claim 1, further comprising the step of injecting cement through the bone fastener into a vertebra of the patient anatomy.

8. A method as recited in claim 1, wherein the bone fastener includes a fenestrated screw.

9. A method as recited in claim 1, wherein the bone fastener includes a sagittally adjustable screw.

10. A method as recited in claim 1, wherein the at least two bone fasteners are connected with one surgical driver and the engaging includes the navigation component of the surgical driver generating a signal representative of the 3D position of each of the at least two bone fasteners relative to the surgical driver and relative to the vertebral tissue.

11. A method as recited in claim 1, wherein the surgical instrument includes a first member and a second member movable relative to the first member, the surgical instrument further includes a ratchet preventing movement of the second member relative to the first member in a first direction and a second direction.

12. A method as recited in claim 1, wherein, prior to imaging the patient anatomy, a reference marker is attached to the patient anatomy.

13. A method as recited in claim 1, further comprising displaying the post-correction orientation of bone fasteners by a computer screen.

14. A method as recited in claim 1 wherein the manipulation strategy comprising manipulating a first of the at least two bone fasteners a selected distance and a selected angular orientation relative to a second of the at least two bone fasteners within the 3D space.

15. A method as recited in claim 1 wherein the manipulation strategy comprises using the reference markers of the at least two bone fasteners to overlay the at least two bone fasteners to the anatomy of the patient.

16. A method as recited in claim 1 wherein the first implant support comprises extender tabs attachable to corresponding tabs of the bone fastener.

17. A method for treating a spine, the method comprising the steps of:
attaching a reference marker to the patient anatomy;
imaging a patient anatomy for registration of anatomical image data and positional tracking of the patient anatomy;
determining an implant strategy for at least two bone fasteners, the implant strategy comprising at least a trajectory to position and engage the at least two bone fasteners to vertebral tissue of a patient;
determining based on the patient anatomy and the implant strategy, a manipulation strategy for the patient anatomy;
determining a post-correction orientation of the patient anatomy according to the implant strategy and the manipulation strategy by calculating the post-correction orientation with a processor configured to implement executable software according to the implant strategy and the manipulation strategy;
imaging the post-correction orientation of the bone fasteners;
connecting the at least two bone fasteners with one surgical driver having a navigation component and engaging the at least one bone fastener with the vertebral tissue of the patient anatomy according to the implant strategy; the navigation component of the surgical driver structured to generate a signal representative of a 3D spatial position of the bone fastener relative to the driver and relative to the vertebral tissue;
injecting cement through the at least one bone fastener into a vertebra of the patient anatomy;
connecting a first implant support to a first of the at least two bone fasteners, the first implant support including an adaptor that is movable relative to the first implant support to releasably engage a surgical instrument to distract and/or compress the vertebral tissue according to the manipulation strategy;

wherein the manipulating strategy comprises manipulating the first of the at least two bone fasteners to a selected angular orientation relative to a second of the at least two bone fasteners to decompress vertebral tissue; and
comparing an actual correction orientation of the patient anatomy according to the manipulation strategy with the determined post-correction orientation.

18. A method as recited in claim 17 wherein manipulation strategy comprises manipulating either or both of the first bone fastener and the second bone fastener such that the relative angle between them is about 7 degrees and such that a distance between them is about 27 mm.

19. A system comprising:
a tangible storage device comprising computer-readable instructions;
an image guide being oriented relative to a sensor for registration of anatomical image data and positional tracking of the patient anatomy; and
a processor, executing the instructions in operation of the system for:
imaging a patient anatomy for registration of anatomical image data and positional tracking of the patient anatomy;
determining an implant strategy for at least two bone fasteners, each of the at least two bone fasteners comprising a reference marker trackable in a 3D space;
the implant strategy comprising at least a trajectory to position and engage the at least two bone fasteners to a vertebral tissue of the patient;
the at least two bone fasteners engageable with a surgical driver comprising a navigation component structured to generate a signal representative of a 3D spatial position of the surgical driver relative to each of the reference markers;
determining, based on the patient anatomy and the implant strategy and a manipulation strategy for a bone fastener connected to an implant support;
the manipulation strategy comprising manipulating at least a first of the at least two bone fasteners a selected distance relative to a second of the at least two bone fasteners;
determining a post-correction orientation of the patient anatomy according to the implant strategy and the manipulation strategy by calculating the post correction orientation with a processor configured to implement executable software according to the implant strategy and the manipulation strategy; and
imaging the post-correction orientation of the patient anatomy.

20. A spinal implant system as recited in claim 19, further comprising a tracking device including a sensor that receives the signal and communicates with the processor to generate data for display of an image from a monitor, the image representing position of the image guide relative to tissue.

* * * * *